US006656192B2

(12) United States Patent
Espositio et al.

(10) Patent No.: US 6,656,192 B2
(45) Date of Patent: Dec. 2, 2003

(54) SITE MARKER DEVICE (75) Inventors: Felix Espositio, Stratford, CT (US); Frank J. Viola, Sandy Hook, CT (US); Mitchell J. Palmer, New Milford, CT (US); John Pellicano, Bethany, CT (US)

(73) Assignee: United States Surgical Corporatioin, Norwalk, CT (US)

( * ) Notice: Subject to any disclaimer, the term of this patent is extended or adjusted under 35 U.S.C. 154(b) by 102 days.

(21) Appl. No.: 09/837,532

(22) Filed: Apr. 18, 2001

(65) Prior Publication Data

US 2001/0023322 A1 Sep. 20, 2001

Related U.S. Application Data

(63) Continuation of application No. PCT/US99/24867, filed on Oct. 22, 1999.
(60) Provisional application No. 60/105,419, filed on Oct. 23, 1998, and provisional application No. 60/101,801, filed on Sep. 25, 1988.

(51) Int. Cl.$^7$ ................................................ A61B 17/00
(52) U.S. Cl. ...................................................... 606/116
(58) Field of Search ............................... 623/1.11, 1.18, 623/1.19, 1.22; 604/117, 51, 164.01, 164.04, 164.11, 164.13; 606/185, 159, 232, 213, 220, 127, 116

(56) References Cited

U.S. PATENT DOCUMENTS

| 67,545 A | 8/1867 | Hodgins |
| 2,514,047 A | 7/1950 | Goforth |
| 3,683,891 A | 8/1972 | Eskridge et al. |
| 3,858,783 A | 1/1975 | Kapitanov et al. |
| 4,011,873 A | 3/1977 | Hoffmeister |
| 4,214,456 A | 7/1980 | Hannum |
| 4,595,007 A | 6/1986 | Mericle |
| 4,795,458 A | * 1/1989 | Regan ............................ 623/1 |
| D304,433 S | 11/1989 | McConnell, Jr. |
| 4,932,962 A | 6/1990 | Yoon et al. |
| 5,053,047 A | 10/1991 | Yoon |
| D324,350 S | 3/1992 | Owens, Jr. |
| 5,197,484 A | 3/1993 | Kornberg et al. |
| 5,221,269 A | 6/1993 | Miller et al. |
| 5,222,976 A | 6/1993 | Yoon |
| 5,531,761 A | 7/1996 | Yoon |
| 5,562,685 A | 10/1996 | Mollenauer et al. |
| 5,582,616 A | 12/1996 | Bolduc et al. |
| 5,607,467 A | * 3/1997 | Froix ............................ 623/1 |
| 5,709,692 A | 1/1998 | Mollenauer et al. |
| 5,772,671 A | 6/1998 | Harmon |
| 5,782,844 A | 7/1998 | Yoon et al. |
| 5,800,445 A | 9/1998 | Ratcliff et al. |
| 5,879,357 A | * 3/1999 | Heaton et al. .............. 606/116 |

* cited by examiner

Primary Examiner—Sharon Kennedy (57) ABSTRACT

A site marker device and marker are provided. The site marker device includes a housing and a distally extending delivery tube. A pusher rod is movably positioned within the delivery tube to eject a marker from the distal end thereof. An elongated tubular body is positioned about the delivery tube. An actuator is provided to provide two stage advancement. During the first stage, the delivery tube and the pusher rod are advanced through the distal end of the elongated tubular body. During the second stage of advancement, the pusher rod is advanced independently of the delivery tube to eject a marker from the distal end thereof. The marker is formed from a shape memory material and has a circular or hoop configuration in the relaxed state.

11 Claims, 10 Drawing Sheets

SITE MARKER DEVICE

CROSS REFERENCE TO RELATED APPLICATION

This application claims priority as a continuation of PCT International Application No. PCT/US99/24867, filed Oct. 22, 1999, and U.S. provisional application Ser. Nos. 60/105,419, filed Oct. 23, 1998, and 60/101,801, filed Sep. 25, 1998, all of which are hereby incorporated by reference.

BACKGROUND

1. Technical Field

The present disclosure relates generally to a marking device for identifying the location of a surgical site and, more specifically, a marking device which is insertable through a biopsy needle to position a marking hoop at a biopsy site.

2. Background of Related Art

Devices for marking lesions within the body are well known in the art. These devices generally include a cannula which is inserted into the body under local anesthesia to a position adjacent and/or in contact with the lesion. A wire marker is passed through the cannula and is anchored to the lesion so that the lesion is marked for subsequent surgical procedures such as excision or biopsy. After marking the lesion, the cannula is usually removed leaving the wire in place and extending from the body.

One problem associated with these devices is that the wire markers tend to dislodge and migrate during transport of the patient to undergo the subsequent surgical procedure.

U.S. Pat. No. 5,018,530 ("the '530 patent") discloses a wire needle assembly designed to overcome this problem. The '530 patent attempts to solve the above-identified problem by providing a marker wire having a helically wound wire tip attached to a shaft which is inserted within the lumen of a cannula and then rotated into a lesion to anchor the marker within the lesion tissue. One disadvantage of the '530 patent wire needle assembly is that the marker wire helix is too large in diameter to fit down the smaller biopsy cannulas. Moreover, some migration of the marker wire may still occur.

U.S. Pat. No. 5,221,269 ("the '269 patent") also discloses a device for marking the locating of a lesion. The device includes an introducer needle and a wire guide which is passed through a passageway in the introducer needle. The wire guide has a straight portion and a distal portion preformed into a resilient helical coil. When positioned in the passageway of the introducer needle, the preformed distal portion assumes an unwound configuration. The wire guide can be advanced distally from the introducer needle to mark the location of a lesion.

One problem associated with the device disclosed in the '269 patent is that there is no structure disclosed for accurately advancing the wire guide into the lesion. Thus, if the wire guide is inserted too deeply into the lesion such that the straight portion extends through the lesion, migration may still occur. Moreover, because the adjacent coils of the helical wire guide are spaced, migration of the wire guide may still occur even if the wire guide is properly positioned.

Accordingly, a need exists for a site marking device for identifying the location of a surgical site or lesion which is capable of accurately positioning a marker which will not migrate adjacent the surgical site.

SUMMARY

In accordance with the present disclosure, a site marker assembly including a site marker device and a marker are provided. The site marker device includes a housing having a bore. A delivery tube is secured to a forward end of the housing and extends distally therefrom. A rod pusher is movably positioned within the delivery tube. An actuator including a plunger is movably positioned within the housing and is operably connected to the rod pusher. The plunger is movable from a first position to a second position to advance the rod pusher through the delivery tube and eject a marker from the distal end of the delivery tube.

In an alternate embodiment, an elongated tubular body is positioned about the delivery tube and the actuator further includes an inner housing movably positioned within the housing. The inner housing defines a bore in which the forward end of the plunger is positioned. The actuator is operably connected to the rod pusher and the delivery tube to provide two stage advancement. During the first stage of advancement, the rod pusher and the delivery tube are advanced through the distal end of the elongated tubular body. During the second stage of advancement, the rod pusher is advanced independently of the delivery tube to eject a marker from the delivery tube.

The marker is formed from a shape memory material such as tinel and has a circular or hoop configuration. The ends of the hoop are closely aligned or stacked to prevent migration of the hoop with respect to a lesion.

BRIEF DESCRIPTION OF THE DRAWINGS

Various preferred embodiments of the site marker device are described herein with reference to the drawings wherein.

DETAILED DESCRIPTION OF PREFERRED EMBODIMENTS

Preferred embodiments of the presently disclosed site marker will now be described in detail with reference to the drawings, in which like reference numerals designate identical or corresponding elements in each of the several views.

Figure 1:
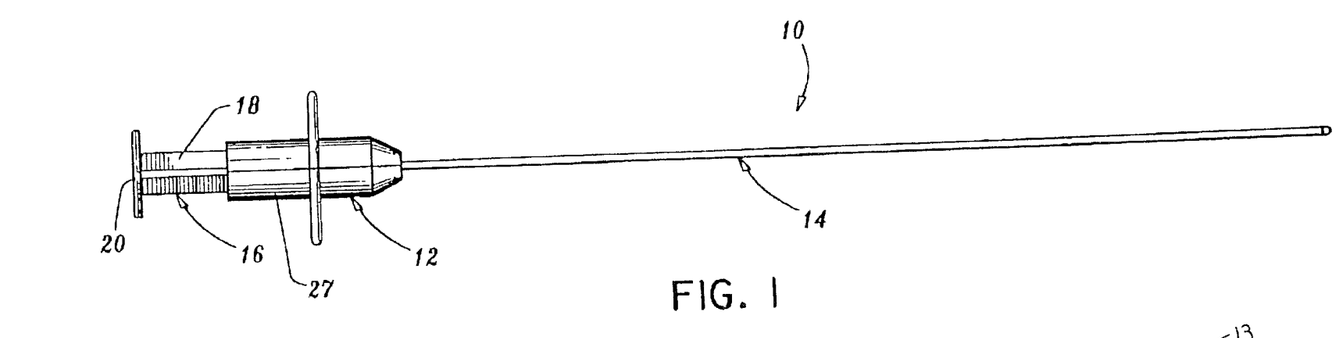
FIG. 1 is a side view of one embodiment of the presently disclosed site marking device in a retracted position.

One embodiment of the presently disclosed site marker will now be described with reference to FIGS. 1–10. FIG. 1 illustrates the site marker device shown generally as 10. Briefly, site marker 10 includes a housing 12, an elongated body 14, and a plunger 16. Elongated body 14 is secured to a forward end of housing 12 and extends distally therefrom. Plunger 16 has a forward end 16a which is slidably positioned within housing 12 and a proximal end 16b which extends outwardly from housing 12 (FIG. 2).

Figure 2:
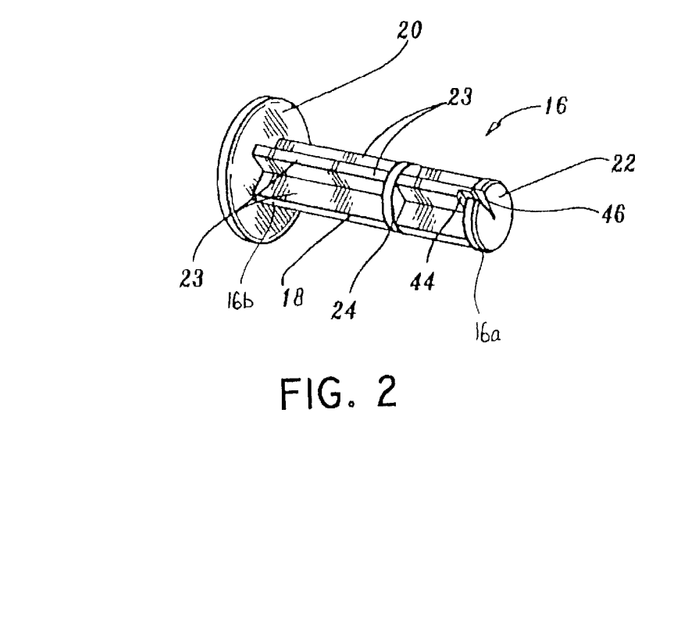
FIG. 2 is a perspective view of the plunger of the site marker device shown in FIG. 1.

Referring to FIG. 2, plunger 16 has t-shaped body 18, a large diameter head portion 20 and a small diameter plunger portion 22. The t-shaped body includes four legs 23, each leg being positioned perpendicular to each adjacent leg. One of the legs has a cutaway portion defining a shoulder 44 which will be discussed in further detail below. Head portion 20 is dimensioned to be engaged by the thumb of a surgeon, while plunger portion 22 is dimensioned and configured to be slidably positioned within housing 12. Plunger portion 22 includes a slot 46 which is aligned with shoulder 44 formed in one of legs 23. An abutment member 24 is positioned along the length of body 18 of plunger 16 to interact with four protrusions 26 formed on housing 12 (FIG. 3) and prevent separation of plunger 16 and housing 12. As illustrated, abutment member 24 includes a cylindrical disc which is oriented perpendicular to the longitudinal axis of each of legs 23. Alternately, the abutment member may have other configurations suitable to prevent separation of the plunger and housing.

Figure 3:
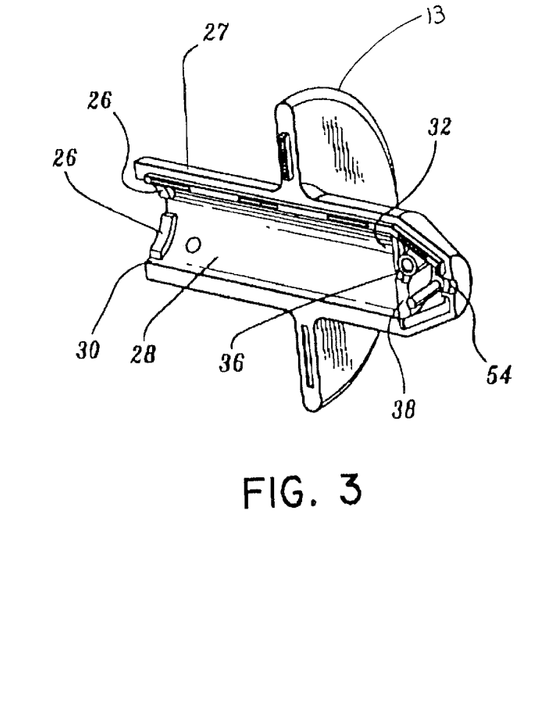
FIG. 3 is a perspective view of a housing half-section of the site marker device shown in FIG. 1.

Referring to FIG. 3, housing 12 is constructed from molded housing half-sections (only one is shown) and has a body 27 which defines a bore 28 having a proximal end 30 and a distal end 32. An annular grasping collar 13 is positioned about body 27. The four protrusions 26 are positioned at spaced locations about proximal end 30 of bore 28. Each protrusion 26 is spaced from adjacent protrusions a distance slightly greater than the width of legs 23 of t-shaped body 18 such that each of the legs can be slidably positioned between the adjacent protrusions. Protrusions 26 prevent rotation of plunger 16 relative to housing 12. Plunger portion 22 is dimensioned to be slidably positioned within bore 28 from a retracted position wherein abutment member 24 abuts protrusions 26 to an advanced position wherein plunger portion 22 engages the distal end of bore 28, which is defined by a transverse wall 38. Transverse wall 38 has a centrally located slot 36 formed therein dimensioned to permit passage of a rod pusher 40 (FIG. 6).

Figure 4:
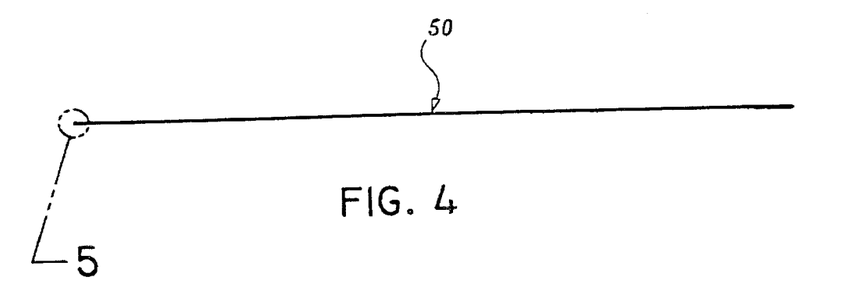
FIG. 4 is a side view of the support tube of the site marker device shown in FIG. 1.
Figure 5:
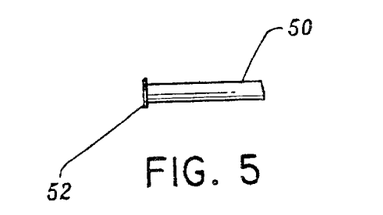
FIG. 5 is an exploded view of the indicated area of detail shown in FIG. 4.

Referring to FIGS. 4 and 5, rod pusher 40 is formed from an elongated spring tempered material, such as metal. The proximal end of the rod pusher has a perpendicular bend 42. Rod pusher 40 is dimensioned to be slidably positioned through slot 36 (FIG. 3) formed in wall 38 of housing 12 and slot 46 (FIG. 2) formed in plunger portion 22 of plunger 16. Perpendicular bend 42 is configured to engage shoulder 44 of plunger 16 such that when the plunger is moved from the retracted to the advanced position, the rod pusher is moved from a retracted to an advanced position.

Figure 6:
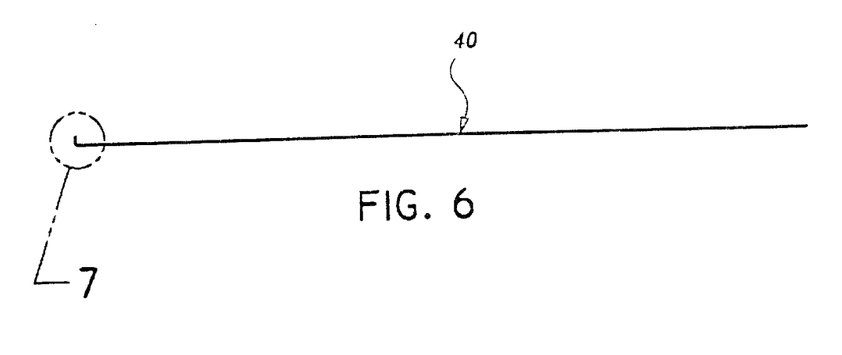
FIG. 6 is a side view of the rod pusher of the site marker device shown in FIG. 1.
Figure 7:
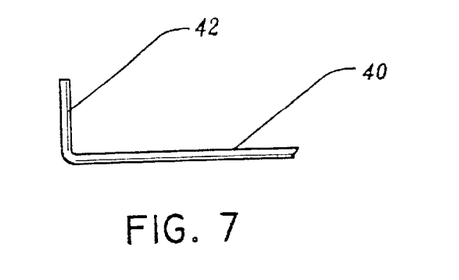
FIG. 7 is an exploded view of the indicated area of detail shown in FIG. 6.

Referring to FIGS. 6 and 7, a small diameter spring tempered support tube 50 has a proximal end having an annular flange 52. Annular flange 52 is dimensioned to be received in an annular slot 54 formed in the forward end of housing 12 (FIG. 3). When flange 52 is positioned within slot 54, relative longitudinal movement of tube 50 in relation to housing 12 is prevented. Support tube 50 has a diameter slightly greater than rod pusher 40 and is positioned about rod pusher 40. The close tolerance between tube 50 and rod pusher 40 prevents buckling of the rod pusher during movement between the retracted and advanced positions.

Figure 8:
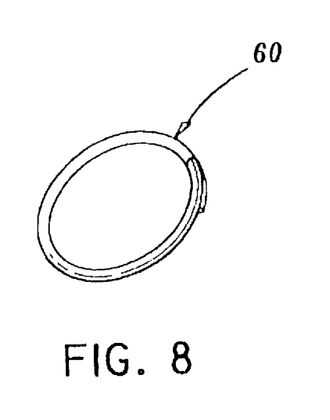
FIG. 8 is a perspective view of the marker used in conjunction with the site marker device shown in FIG. 1.
Figure 9:
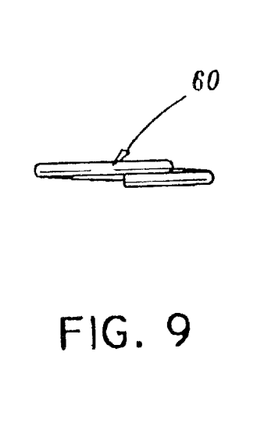
FIG. 9 is a side view of the marker used in conjunction with the site marker device shown in FIG. 1.

Referring to FIGS. 8 and 9, a marker 60 having a substantially circular or hoop configuration formed of shape memory material, such as tinel, is straightened and positioned in the distal end of support tube 50 at a location forward of the distal end of rod pusher 40. During actuation of site marker 10, plunger 16 is moved from the retracted to the advanced position by grasping collar 13 of housing 12 and pressing on head portion 20 of plunger 16. As the plunger slides within bore 28, rod pusher 40 is advanced distally within support tube 50, such that the distal end of rod pusher 40 engages marker 60 and urges marker 60 out of the distal end of support tube 50. As the marker exits the distal end of tube 50, the marker returns to its normal circular or hoop configuration.

Figure 9A:
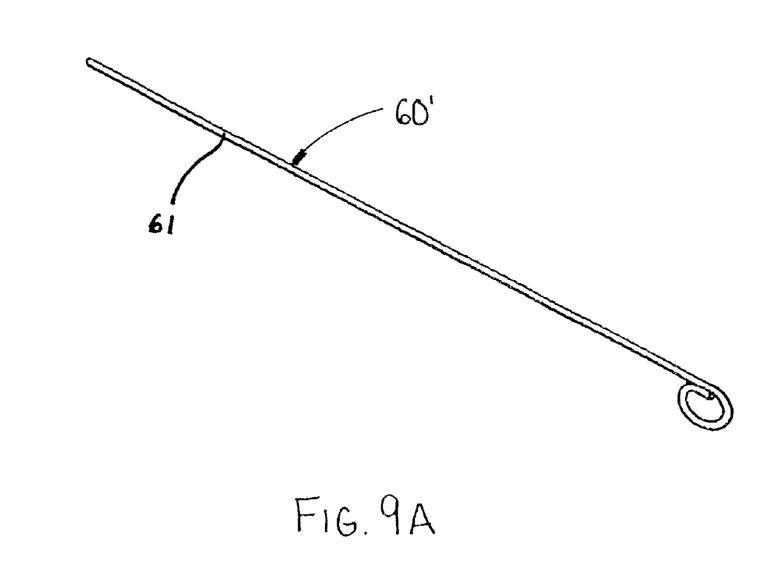
FIG. 9A is an alternate embodiment of the marker shown in FIG. 9.
Figure 10:
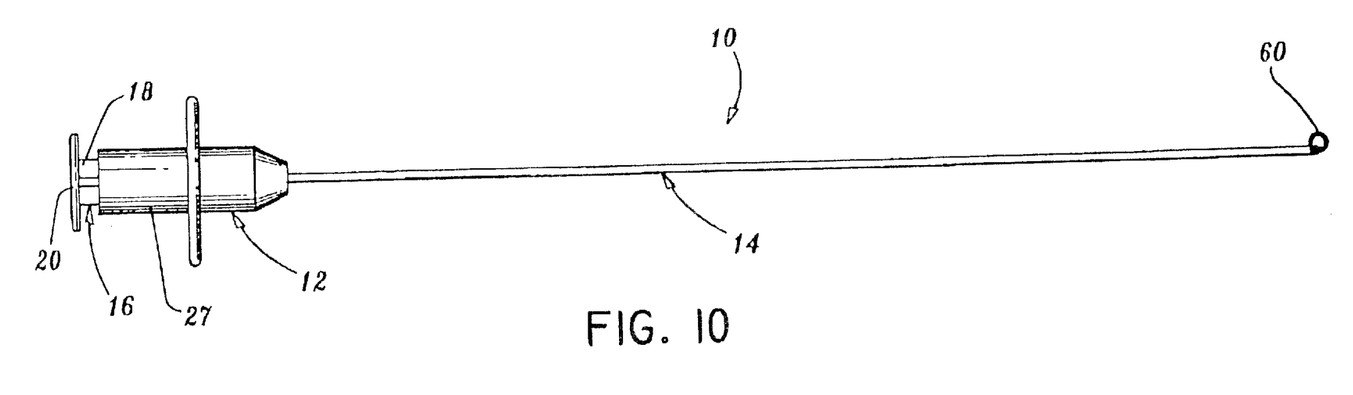
FIG. 10 is a side view of the site marking device shown in FIG. 1 in an advanced or actuated position.

In an alternate embodiment illustrated in FIG. 9A, marker 60' can include a substantially straight tail section 61. Tail section 61 is of a length to extend from the body of a patient after marker 60 has been positioned adjacent a biopsy site. When using marker 60' having a tail section 61, rod pusher 40 must be shortened accordingly.

Figure 11:
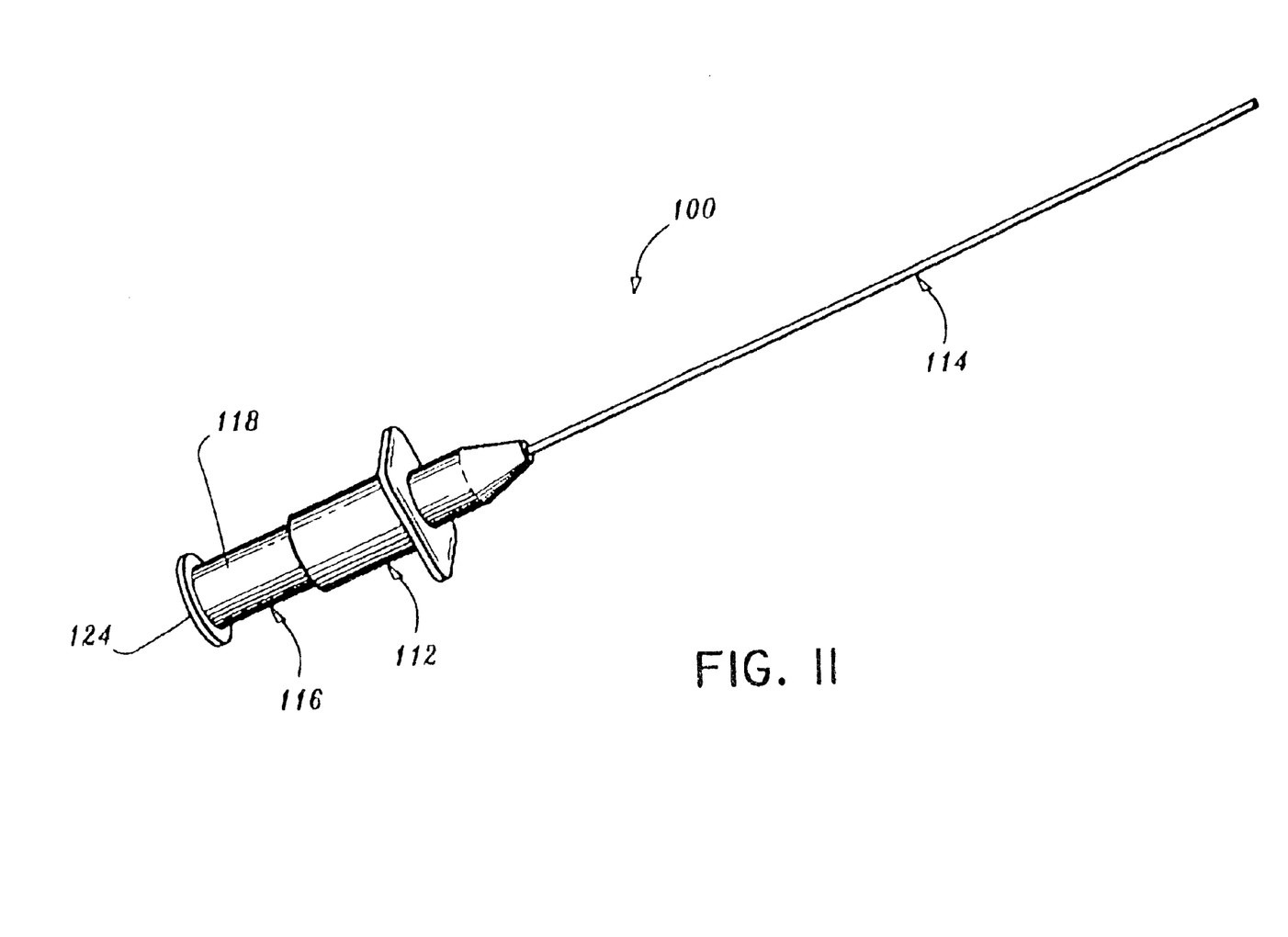
FIG. 11 is a perspective view of another embodiment of the presently disclosed site marker device.

FIGS. 11–16 illustrate an alternate embodiment of the site marker device shown generally as 100. FIG. 11 illustrates a perspective view of site marker 100. Briefly, site marker device 100 includes a housing 112 having a guide tube 114 extending distally from a forward end thereof. A plunger 116 having a cylindrical cover 118 is slidably positioned within a cylindrical bore (not shown) formed within housing 112 and includes a proximal end 112a extending from a rearward end of housing 112. A coupler 120 is secured to the distal end of guide tube 114 using known techniques, e.g., crimping, adhesives, welding, etc. Coupler 120 is adapted to receive a diverter 122 which will be discussed in further detail below. It is also envisioned that site marker device 100 be used without coupler 120 and diverter 122.

Figure 12:
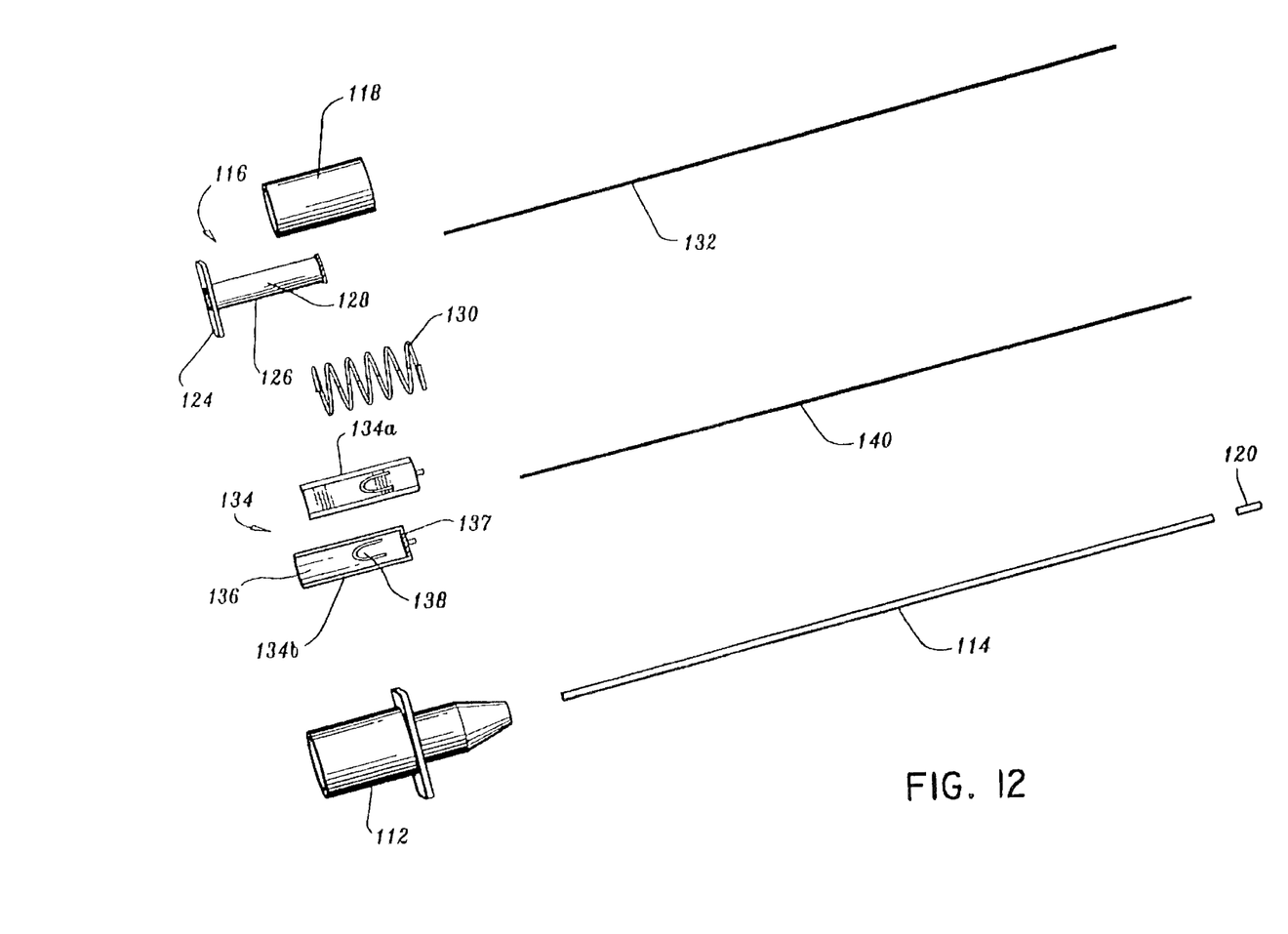
FIG. 12 is a perspective view with parts separated of the site marker device shown in FIG. 11.

Referring to FIG. 12, plunger 116 includes a large diameter head portion 124 dimensioned to be engaged by the thumb of a surgeon and a plunger portion 126 dimensioned to be positioned within housing 112. The plunger is slidable within housing 112 from a retracted position to an advanced position. A biasing member 130, which is preferably a coil spring, is positioned between head portion 124 and the end of the bore defined within housing 112 to urge the plunger to the retracted position. Plunger 116 includes an annular rib 128 which will be discussed in further detail below. A rod pusher 132 is secured to the plunger portion 126 of plunger 116 using known techniques, e.g., pins, threads, crimping, annular flange, etc. Rod pusher 132 is formed from a small diameter spring tempered material such as metal and is movable from a retracted to an advanced position in response to movement of the plunger from the advanced to the retracted position. Alternately, other resilient materials may be used to form the rod pusher.

An inner housing 134, which is preferably formed from molded housing half-sections 134a and 134b, is positioned about plunger 116 and slidably positioned within the bore (not shown) defined within housing 112. Inner housing 134 defines a second bore 136 within which plunger portion 126 of plunger 116 is positioned. Bore 136 of inner housing 134 includes a forward wall 137 and a pair of detents 138 formed on opposite walls thereof. Detents 138 are positioned to engage annular rib 128 on plunger 116 to prevent plunger portion 126 from moving into engagement with wall 137 of bore 136 until after a predetermined force sufficient to move rib 128 over detents 138 has been applied to plunger 116. Thus, when the plunger 116 is in the retracted position, plunger portion 126 of plunger 116 is spaced from wall 137 of bore 136 a predetermined distance.

A delivery tube 140 is secured to a forward end of inner housing 134 using known techniques, e.g., crimping, threads, etc. Preferably, the proximal end of delivery tube 140 includes an annular flange such as shown in FIG. 5 which is received in an annular slot formed in the distal end of inner housing 134 to secure the delivery tube to the inner housing. The delivery tube 140 is preferably formed from spring tempered material such as metal and has an inner diameter dimensioned to permit rod pusher 132 to slide therein. The inner diameter of delivery tube 140 is only slightly larger than the outer diameter of rod pusher 132 to prevent buckling of the rod pusher 132 as it is moved from the retracted to the advanced position.

Figure 13:
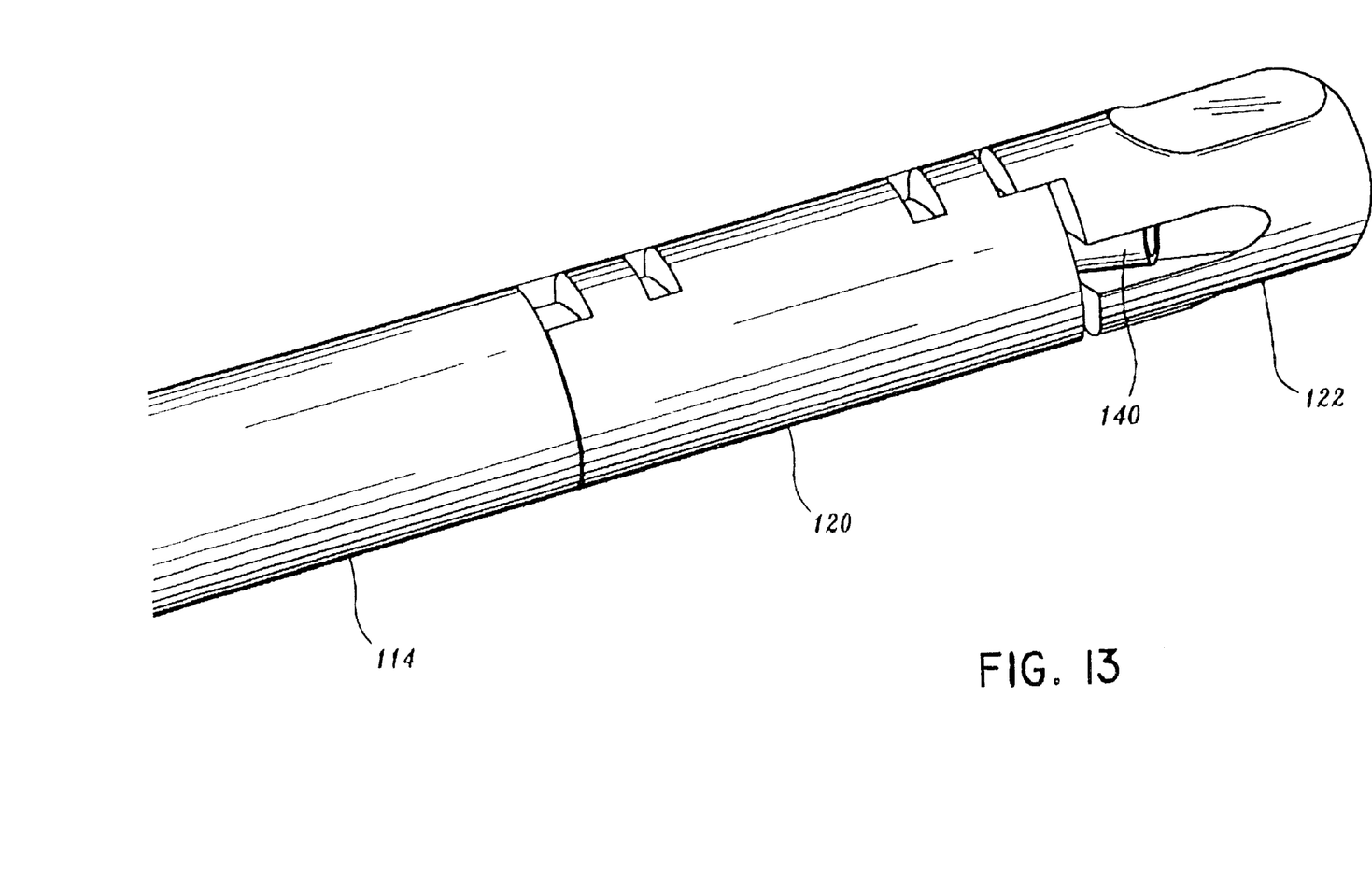
FIG. 13 is a perspective view of the distal end of the site marker device shown in FIG. 11 in the retracted position.

As discussed above, coupler 120 and a diverter 122 are secured to the distal end of guide tube 114. As illustrated in FIG. 13, diverter 122 has a curved channel 150 extending therethrough. In the retracted position of plunger 116, the distal end of delivery tube 140 is positioned partially within curved channel 150.

Marker 160 is positioned in the distal end of delivery tube 140 at a location forward of the distal end of rod pusher 132. Marker 160 is formed from shape memory material, such as tinel, and has a relaxed substantially circular or hoop configuration. Alternately, a marker having a tail section, such as illustrated in FIG. 8A may also be used.

Figure 14:
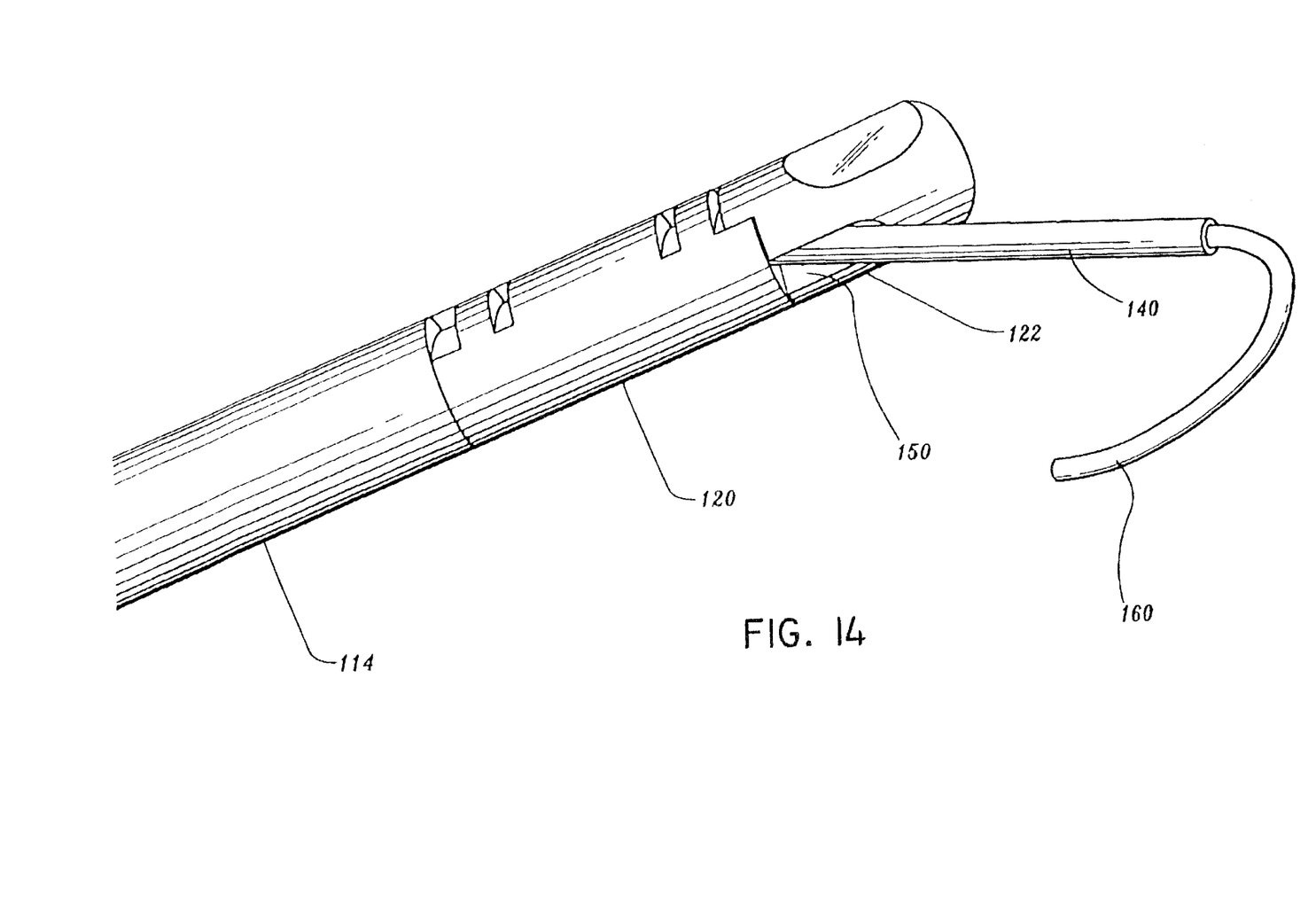
FIG. 14 is a perspective view of the distal end of the site marker device shown in FIG. 11 in a partially advanced position.
Figure 15:
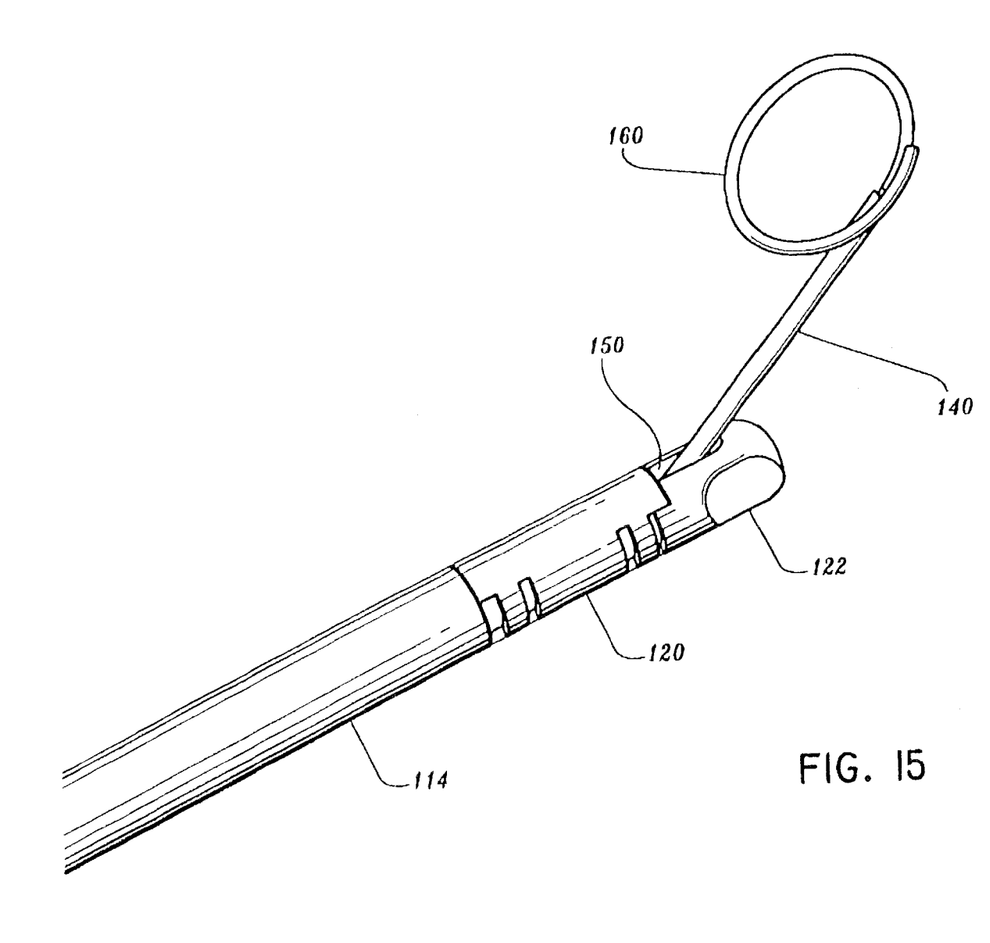
FIG. 15 is a perspective view of the distal end of the site marker device shown in FIG. 11 in the advanced position.
Figure 16:
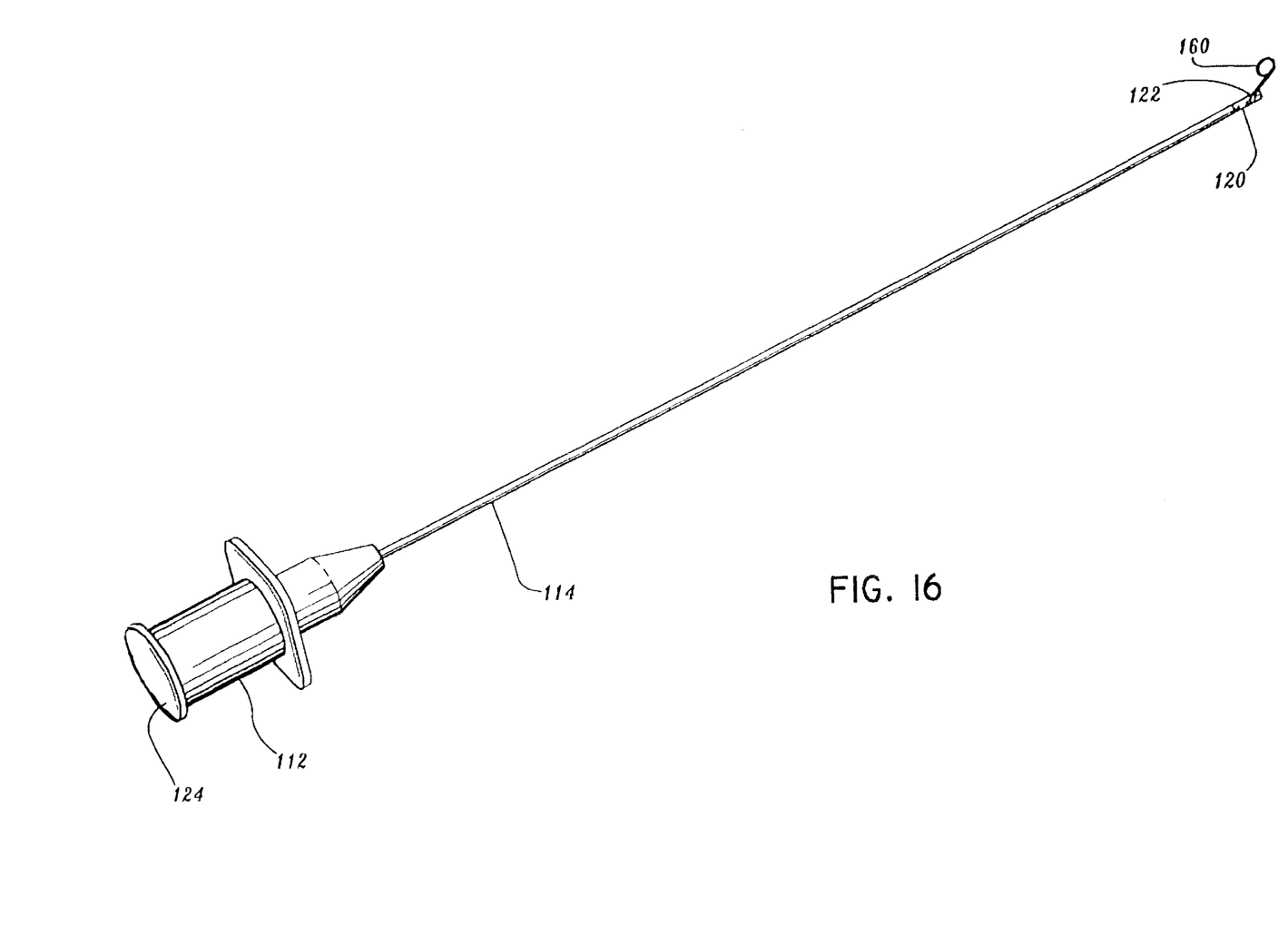
FIG. 16 is a perspective view of the site marker device shown in FIG. 11 in the advanced position.

Referring to FIG. 14, during the initial movement of plunger 116 from the retracted position towards the advanced position, plunger 116 advances inner housing 134 distally within the housing bore (not shown) formed within housing 112. Plunger 116 and inner housing 134 will move together until the forward end of inner housing 134 abuts against the base of the bore defined by housing 112. At this point, the delivery tube 140 has been advanced through curved channel 150 formed in diverter 112 and is angled outwardly and spaced from the distal end of guide tube 114. Rod pusher 132 has not yet been moved relative to delivery tube 140 and marker 160 is still positioned in the distal end of delivery tube 140.

Referring to FIG. 14, when a predetermined force sufficient to advance annular rib 128 over detents 138 is applied to plunger 116, plunger 116 moves within bore 136 of inner housing 134 to move rod pusher 132 within delivery tube 140. The distal end of rod pusher 132 engages marker 160 and urges marker 160 out of the distal end of delivery tube 140. As marker 160 is ejected from delivery tube 140, marker 160 will return to the relaxed state in which the marker has a substantially circular or hoop configuration. See FIGS. 15 and 16.

Site marker device 100 may be used in conjunction with the biopsy apparatus and method disclosed in U.S. patent application Ser. No. 09/040,244 filed Feb. 20, 1998, currently pending ('244 application) which is incorporated herein by reference.

It will be understood that various modifications may be made to the embodiments disclosed herein. For example, the actuator need not be a plunger-type actuator but rather may be a trigger-type actuator or other known actuation mechanism. Moreover, the site marker device can be constructed from a variety of materials having the requisite strength and resiliency characteristics including plastics and metals. Therefore, the above description should not be construed as limiting, but merely as exemplifications of preferred embodiments. Those skilled in the art will envision other modifications within the scope and spirit of the claims appended hereto.

What is claimed is:

1. A site marker device comprising:
   an outer housing;
   a delivery tube supported by the outer housing and extending distally therefrom, the delivery tube having an internal diameter dimensioned to receive a marker;
   a pusher rod positioned within the delivery tube;
   an actuator supported by the housing, the actuator being movable from a first position to a second position to effect movement of the pusher rod from a retracted position to an advanced position;
   wherein the outer housing defines a bore and the actuator includes a plunger including a plunger portion slidably positioned within the bore; and
   wherein the delivery tube includes a proximal end and a distal end, the proximal end having an annular flange positioned within a slot formed in the outer housing.

2. A site marker device comprising:
   an outer housing;
   a delivery tube supported by the outer housing and extending distally therefrom, the delivery tube having an internal diameter dimensioned to receive a marker;
   a pusher rod positioned within the delivery tube;
   an actuator supported by the housing, the actuator being movable from a first position to a second position to effect movement of the pusher rod from a retracted position to an advanced position;
   wherein the outer housing defines a bore and the actuator includes a plunger including a plunger portion slidably positioned within the bore; and
   wherein the pusher rod has a proximal end and a distal end, the proximal end having a bend formed therein, the bend operably engaging the plunger such that movement of the plunger effects corresponding movement of the pusher rod.

3. A site marker device comprising:
   an outer housing;
   a delivery tube supported by the outer housing and extending distally therefrom, the delivery tube having an internal diameter dimensioned to receive a marker;
   a pusher rod positioned within the delivery tube;
   an actuator supported by the housing, the actuator being movable from a first position to a second position to effect movement of the pusher rod from a retracted position to an advanced position;
   wherein the actuator includes a plunger having a plunger portion movable within the outer housing, the pusher rod being operably connected to the plunger; and
   including an elongated tubular body secured to the outer housing and extending distally therefrom, the elongated tubular body being positioned about the delivery tube.

4. A site marker device according to claim 3, wherein the actuator further includes an inner housing movably positioned within the outer housing, the inner housing defining a bore, wherein the plunger portion of the plunger is slidably positioned within the bore.

5. A site marker device according to claim 4, wherein the inner housing bore includes at least one detent, the at least one detent preventing linear movement of the plunger in relation to the inner housing until a predetermined force by the plunger on the at least one detent is reached, wherein during a portion of movement of the actuator from the first to the second position, the pusher rod and the delivery tube are simultaneously advanced until the predetermined force is reached, thereafter the pusher rod is advanced independently of the delivery tube.

6. A site marker device according to claim 5, further including a diverter secured to the distal end of the elongated tubular body, the diverter having a curved channel formed therein and being positioned to direct the delivery tube at a predetermined angle outwardly of the elongated tubular body.

7. A site marker device according to claim 6, wherein the delivery tube and the rod pusher are formed from a spring tempered material.

8. A site marker assembly comprising:
   a) a site marker device having an outer housing, a delivery tube supported by the outer housing, a pusher rod movably positioned within the delivery tube, and an actuator supported by the outer housing and movable from a first position to a second position to move the pusher rod from a retracted position to an advanced position; and
   b) a marker constructed from shape memory material and having a relaxed hoop configuration, the marker being dimensioned to be received within the delivery tube.

9. A site marker assembly according to claim 8, wherein the shape memory material is tinel.

10. A site marker assembly according to claim 9, wherein the marker further includes a straight tail section.

11. A method of marking the location of a lesion, the method comprising the following steps:
   a) providing a site marker device having a delivery tube and a pusher rod movably positioned within the delivery tube;
   b) providing a marker formed of shape memory material and having a substantially circular configuration;
   c) deforming the marker and positioning the marker in one end of the delivery tube; and
   d) advancing the pusher rod to eject the marker from the distal end of the delivery tube such that the marker returns to the substantially circular configuration.

* * * * *